(12) United States Patent
Ashburn

(10) Patent No.: US 8,905,730 B2
(45) Date of Patent: Dec. 9, 2014

(54) PERISTALTIC PUMP

(75) Inventor: Nancy Ashburn, Cornwall (GB)

(73) Assignee: Watson-Marlow Limited, Cornwall (GB)

( * ) Notice: Subject to any disclaimer, the term of this patent is extended or adjusted under 35 U.S.C. 154(b) by 287 days.

(21) Appl. No.: 13/148,882

(22) PCT Filed: Feb. 10, 2010

(86) PCT No.: PCT/GB2010/050215
§ 371 (c)(1),
(2), (4) Date: Oct. 14, 2011

(87) PCT Pub. No.: WO2010/092385
PCT Pub. Date: Aug. 19, 2010

(65) Prior Publication Data
US 2012/0027622 A1 Feb. 2, 2012

(30) Foreign Application Priority Data

Feb. 10, 2009 (GB) .................................. 0902177.5

(51) Int. Cl.
F04B 43/12 (2006.01)
A61M 5/142 (2006.01)
A61M 39/08 (2006.01)

(52) U.S. Cl.
CPC ............ *F04B 43/12* (2013.01); *A61M 5/14232* (2013.01); *A61M 39/08* (2013.01); *A61M 2205/3569* (2013.01); *A61M 2205/3592* (2013.01); *A61M 2205/6054* (2013.01)
USPC .............................. 417/477.1; 417/53; 417/63

(58) Field of Classification Search
CPC ............ A61M 5/14232; A61M 39/08; A61M 2205/3592; A61M 2205/3576; F04B 43/12
USPC ........................................... 417/53, 63, 477.1
See application file for complete search history.

(56) References Cited

U.S. PATENT DOCUMENTS 6,626,355 B2    9/2003  Sasse et al.
7,661,582 B2 *  2/2010  Mollstam ..................... 235/375

(Continued)

FOREIGN PATENT DOCUMENTS

EP    0682952 A1    11/1995
EP    0776670 A2    6/1997

(Continued)

OTHER PUBLICATIONS

International Search Report dated Jul. 8, 2010 for PCT/GB2010/050215.

(Continued)

*Primary Examiner* — Peter J Bertheaud
*Assistant Examiner* — Dominick L Plakkottam
(74) *Attorney, Agent, or Firm* — Honigman Miller Schwartz and Cohn LLP

(57) ABSTRACT

A peristaltic pump comprises a pump unit including a pump which receives a replaceable tube. The tube has a transponder, for example an RFID tag, which carries data relating to the tube, which can be read by a reader of the pump unit. On the basis of a comparison between the tube data on the RFID tag and control data held in a memory of the reader, the reader permits operation of the pump unit if the tube data is compatible with the control data, but prevents such operation if the tube data is incompatible with the control data, for example indicting that an incorrect tube has been fitted, or the tube is approaching the end of its predicted operational life.

18 Claims, 4 Drawing Sheets

(56) References Cited

U.S. PATENT DOCUMENTS

| | | | |
|---|---|---|---|
| 2003/0149401 A1* | 8/2003 | Benetti Diaz De Brito et al. | 604/113 |
| 2006/0058804 A1* | 3/2006 | Mollstam | 606/80 |
| 2006/0073048 A1* | 4/2006 | Malackowski | 417/474 |
| 2007/0217933 A1 | 9/2007 | Haser et al. | |
| 2008/0031740 A1 | 2/2008 | Miyazaki et al. | |
| 2008/0130706 A1* | 6/2008 | Kellner et al. | 374/45 |
| 2008/0138218 A1 | 6/2008 | Miyazaki et al. | |
| 2009/0036873 A1* | 2/2009 | Nielsen et al. | 604/543 |
| 2011/0076666 A1* | 3/2011 | Brassil | 435/1.2 |

FOREIGN PATENT DOCUMENTS

| | | | |
|---|---|---|---|
| EP | 1132102 | A2 | 9/2001 |
| EP | 1576971 | A1 | 9/2005 |
| JP | 2004-187942 | A | 7/2004 |
| WO | WO-2004033024 | A1 | 4/2004 |
| WO | WO-2004108189 | A2 | 12/2004 |
| WO | WO-2006036600 | A1 | 4/2006 |

OTHER PUBLICATIONS

U.K. Search Report for Application GB0902177.5 dated Jun. 4, 2009.

U.K. Examination Report for Application GB0902177.5 dated Sep. 13, 2013.

Japanese Office Action along with its English translation thereof dated Dec. 3, 2013 for Application No. 2011-549671.

* cited by examiner

PERISTALTIC PUMP

This invention relates to a peristaltic pump, and to a system including a peristaltic pump.

A peristaltic pump comprises a pump unit and a tube which is removably fitted into the pump unit. The pump unit has drive means, for example a motor-driven rotor having at least one lobe which presses the tube against an arcuate track to perform a peristaltic action on the tube. Fluid is thus displaced through the tube from an inlet to an outlet.

It is important to ensure that the tube fitted to the pump unit has the correct physical characteristics for the pumping operation to be performed. Different pump units require tubes having different physical characteristics such as length, diameter and wall thickness if they are to operate properly. Also, the material of the tube needs to be compatible with the material to be pumped.

Furthermore in some circumstances, for example in medical or food applications, it is vital that the tube is adequately sterilized, for example by autoclaving, before operation of a pump unit in which the tube is fitted.

Failure of a tube during operation of a peristaltic pump can have serious consequences, and it is therefore useful to replace the tube when it is close to the end of its expected life.

Currently, these matters are dealt with using the skill and experience of the operator of the pump. Nevertheless errors sometimes occur with possibly serious consequences. It is therefore desirable for failures due to operator error to be minimised as far as possible.

WO2006036600 discloses a pump comprising a tube set provided with an integral RFID having a memory for storing data, such as run time data, about the tube set. The tube set is inserted into a control module which interrogates the memory to determine, amongst other things, whether the tube set is suitable for use.

According to a first aspect of the present invention there is provided a peristaltic pump comprising a pump unit and a tube mounted in the pump unit, the pump unit having drive means for deforming the tube to perform a peristaltic action, the tube being provided with a transponder having a memory and means for transmitting tube data stored in the memory, and the pump unit having a reader for reading tube data transmitted from the transponder, wherein the reader has a control data memory adapted to store control data relating to the tube, including data representing the predicted operational life of the tube based on the average operational life for other tubes previously operated for their full operational life in the same environment, and means for updating the predicted operational life to include the operational life of the tube mounted in the pump unit.

The reader may be connected to operating means of the pump unit so that operation of the pump unit is controlled in response to tube data transmitted from the transponder.

The tube data may comprise data representing:
The identity of the tube;
The size of the tube, including the internal/external diameter of the tube or the tube length;
The maximum pressure rating of the tube;
The expiry date of the tube;
The lot number of the tube;
The maximum number of autoclave cycles of the tube;
The default calibration of the tube;
The run-time of the tube.

The operating means may then be controlled in response to a comparison of the tube data transmitted from the transponder with the control data stored in the memory of the reader.

The operating means may prevent operation of the drive means if the tube data is incompatible with the control data.

The control data may comprise one or more of:
Data relating to the identity of the tube
Data relating to processes conducted on the tube.

The reader may be provided with transmitting means for transmitting tube data and the transponder may be adapted to receive and store tube data transmitted from the reader. In one embodiment, the reader may be adapted to receive operation data from the operating means, and to convert the operation data to tube data which is transmitted to the transponder by the transmission means of the reader. For example, the operation data may comprise data relating to the duration, speed of operation, pressure and flow rate of the pump while the tube is fitted to the pump unit. The control data may then include data generated as a function of the operation data to represent tube usage so that the memory of the transponder can be supplied with tube data representing cumulative usage of the tube, to enable comparison with the control data to determine when the tube is reaching the end of its expected life, and so should be replaced.

According to a second aspect of the present invention there is provided a peristaltic pump system comprising a peristaltic pump as defined above and tube processing equipment for performing a process on the tube, the tube processing equipment having a data writer for transmitting process data to the memory of the transponder of the tube, the process data being readable by the reader for comparison with the control data.

The tube processing equipment may, for example, be molding equipment, for manufacturing the tube, or tube sterilizing equipment such as an autoclave.

The present invention also provides a tube suitable for use in a peristaltic pump or peristaltic pump system as defined above.

According to a third aspect of the present invention there is provided a method of operating a peristaltic pump according to the first aspect of the invention, or a peristaltic pump system according to the second aspect of the invention, the method comprising the steps of:
(a) installing the tube in the pump unit so that the transponder and the reader are in communication with each other;
(b) transmitting tube data from the transponder to the reader;
(c) updating an accumulated operating time of the tube during operation of the pump;
(d) operating the peristaltic pump until the tube reaches the end of its operational life; and
(e) following the completion of step (d), updating a predicted operational life stored in the control data memory based on the operational life of the tube and of tubes previously operated for their full operational life in the same environment.

Step (e) may comprise updating the predicted operational life only when the operational life of the tube falls outside a predetermined range based on the predicted operational life held in the control data memory.

The previously operated tubes may be tubes previously installed in and operated by the pump unit.

The predicted operational life may be calculated as the average operational life of at least some of the previously operated tubes.

Step (b) may comprise the step of transmitting tube data representing an accumulated operating time of the tube.

The term "operating environment" may refer to type of fluid pumped through the tube and the properties of the fluid such as temperature and pressure, the atmosphere within which the pump unit operates, or treatment of the tube, for example, the stress experienced by the tube.

For a better understanding of the present invention, and to show more clearly how it may be carried into effect, reference will be made by way of example, to the accompanying drawings, in which.

Figure 1:
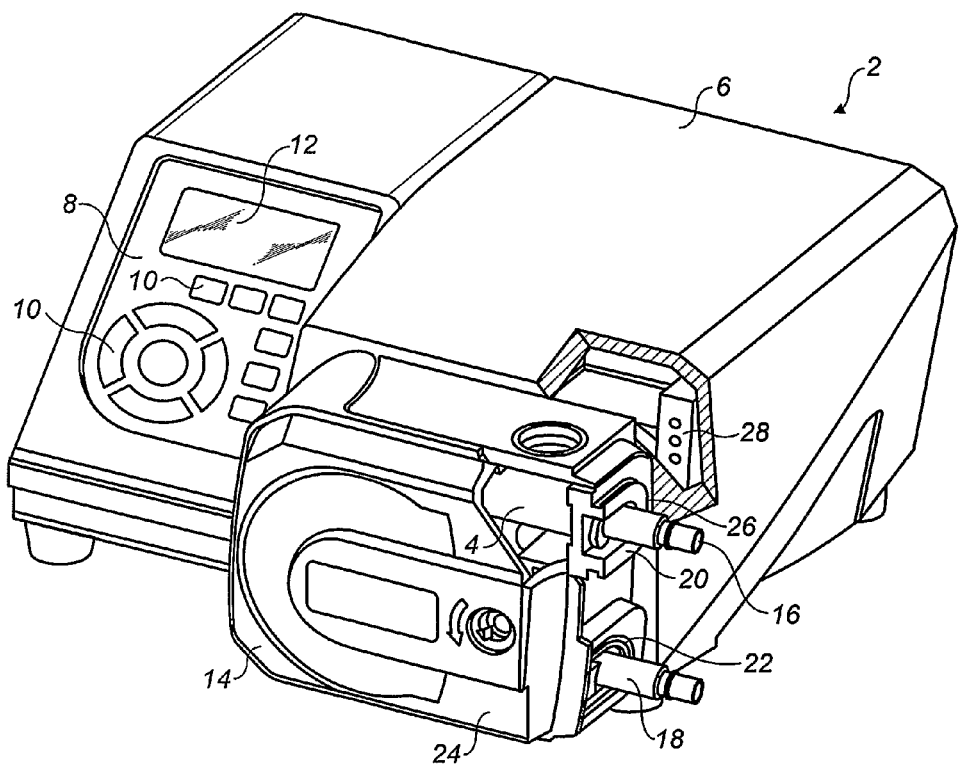
FIG. 1 shows a peristaltic pump.

The pump shown in FIG. 1 comprises a pump unit 2 provided with a tube 4, the pump unit 2 comprises a housing 6 accommodating a drive motor and control circuitry for the pump. One wall of the housing 6 has a control panel 8 with input keys 10 and a display screen 12.

The pump unit 2 also has a pumphead 14 in which the tube 4 is accommodated. The pumphead 14 has a rotor (not shown) which is driven by the motor in the housing 6. In known fashion the rotor has lobes which squeeze the tube 4 against a half-circular track over which the tube 4 runs. This creates a peristaltic action in the tube 4, displacing fluid along it between an inlet end 16 and an outlet end 18 of the tube 4.

The tube 4 is part of an integral tube assembly, which also comprises retaining fittings 20, 22. The retaining fittings 20, 22 are received in complementary recesses in a wall of the pumphead 14. A lid 24 closes over the tube 4 to retain the fittings 20, 22 in the recesses.

Figure 3:
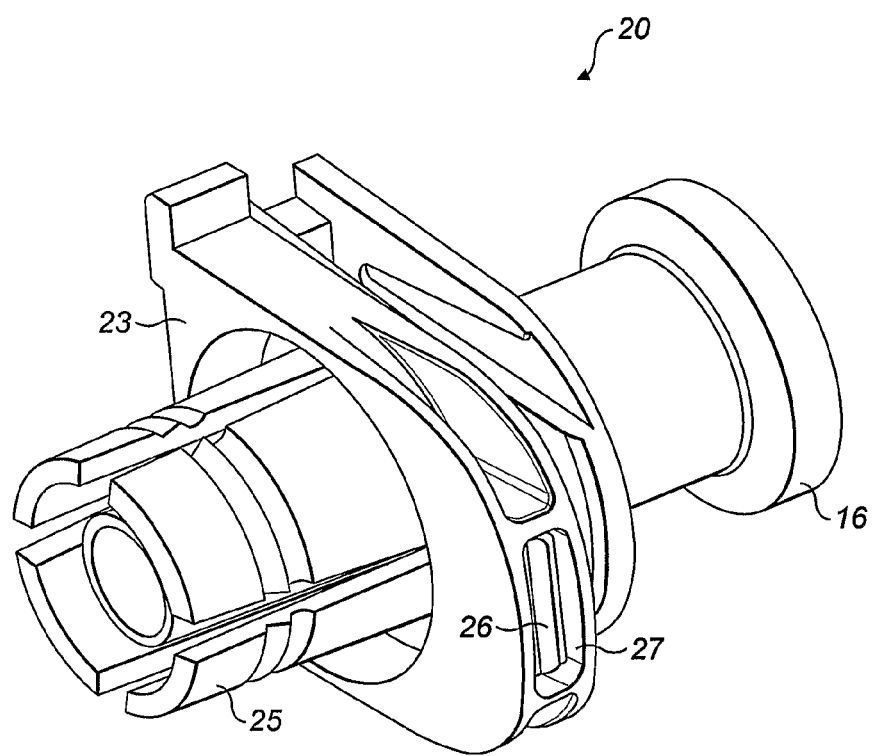
FIG. 3 shows a retaining fitting of the peristaltic pump of FIG. 1.
Figure 4:
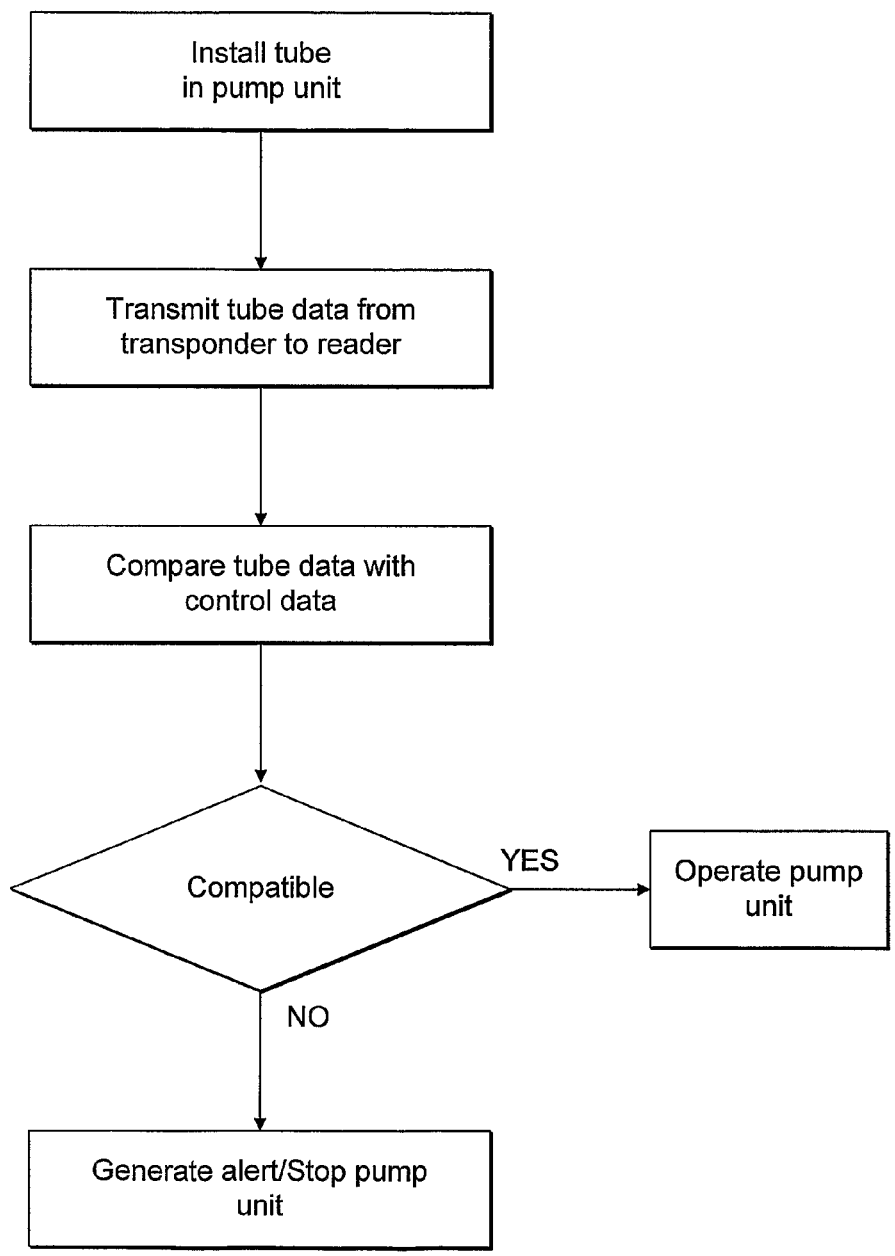
FIG. 4 shows a flow chart for a first method of operating a peristaltic pump.
Figure 5:
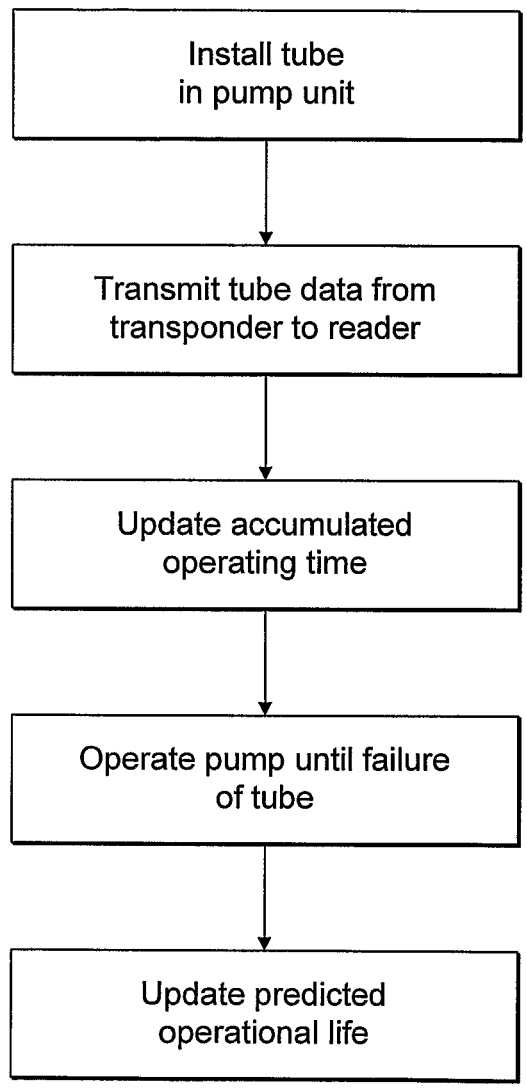
FIG. 5 shows a flow chart for a second method of operating a peristaltic pump.

As shown in FIG. 3, the fitting 20 on the inlet end of the tube 4 comprises a flange 23 for engagement with the wall 24. The flange 23 has a tube coupling 25 on one side which is permanently secured to the tube 4. On the other side, the flange 23 has a connector constituting the inlet end 16 of the tube 4. The flange 23 has a recess 27 which accommodates a removable transponder 26 in the form of an RFID (radio frequency identification device) tag 26. A corresponding reader 28 is provided within the pump unit 2, for example within the housing 6 at a position adjacent to the pumphead 14. It will be appreciated that, when the tube assembly including the tube 4 and the fittings 20. 22 is installed in the pump unit, the transponder 26 is situated close to the reader 28, so that reliable signal transmission between them can take place.

Figure 2:
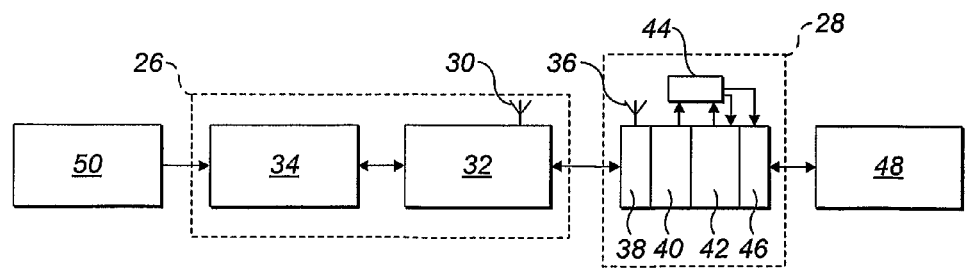
FIG. 2 is a block diagram representing the operation of a system including the peristaltic pump of FIG. 1.

In the embodiment shown schematically in FIG. 2, the RFID tag 26 is of generally known configuration, comprising an antenna 30, radiofrequency transmitting and receiving circuitry 32, and a data storage memory 34. The reader 28 also comprises an antenna 36 and radiofrequency transmitting and receiving circuitry 38. In addition, it has a data storage memory which is represented in FIG. 2 as comprising two sections 40 and 42 for storing respectively, transient tube data received from the RFID tag 26 on the tube 4, and fixed control data 42. The reader 28 also has a comparator 44 for comparing tube data and control data in the memory sections 40, 42. The comparator 44 comprises a processor for processing data received from the memory sections 40, 42. Finally the reader 28 includes control circuitry 46 which receives output from the comparator 44 for controlling operating means 48 of the pump. Although the reader 28 is represented as an integrated unit comprising all of the components 36 to 46, it will be appreciated that, in some embodiments, some functions of the reader 28 may be performed by separate components situated externally of the reader 28 itself.

The operating means 48 comprises the motor driving the rotor of the pumphead 14, and the control circuitry which can be controlled by means of the keypad 10.

Also shown in FIG. 2 is tube processing equipment 50, which may, for example, be an autoclave, which is capable of writing data to the memory 34 of the RFID tag 26 on the tube 4. Thus, the autoclave 50 may have an integral internal writer for writing the data, or there may be an external writer standing alongside the autoclave.

In operation, when a new tube 4 is fitted to the pumphead 14 a sequence of communication between the RFID tag 26 on the tube 4 and the reader 28 within the casing 6 is initiated. For example, on start-up of the pump, the screen 12 may display a message such as "NEW TUBE FITTED?" to which an appropriate yes/no response may be input by way of the keypad 10. If a new tube has been fitted the reader 28 interrogates the RFID tag 26 to establish the identity of the tube, by way of data transmitted by the RF circuitry 32 from the memory 34. Such data may, for example, include an indication of the type of tube 4 that has been fitted which will indicate to the reader 28 the material of the tube, as well as its physical dimensions. In addition, the data may include an individual identification, such as serial number, of the tube 4 as well as other data unique to the individual tube 4, such as its sterilization status and the duration and intensity of previous use of the tube 4.

The data from the RFID tag 26 is stored in the tube data memory 40. By way of the keypad 10 the reader 28 may receive data relating to the pumping operation to be performed by the pump, for example the nature of the fluids to be pumped along with the flow rate and delivery pressure required. On the basis of this information, the reader 28 can address the data stored in the control data memory section 42 and extract values relating to parameters of the tube 4 required for such a pumping operation as well as data relating to the predicted operational life of such a tube. The operational life is defined as the accumulated operating time of the tube 4 up to failure of the tube 4. Failure of a tube 4 is the point at which the tube 4 is no longer suitable for use. Determination of failure can be based on data obtained during use or by inspection of the tube 4 during or after use. For example, an operator may visually inspect the tube 4 to determine whether the amount of wear of the tube 4 is unacceptable or to identify damage to the tube.

In this embodiment, the predicted operational life of the tube 4 is calculated using data stored in the control data memory section 42 representing the operational life of tubes previously fitted to the pumphead 14 which were operated in the same operating environment as the installed tube 4. The predicted operational life may, for example, be calculated as an average operational life of a set number of preceding tubes. It will be appreciated that the set number of tubes need not be consecutively fitted tubes.

Corresponding tube data from the memory 40 is also passed to the comparator 44 which then compares the data received from the RFID tag 26 with that received from the control data memory section 42.

If the tube 4, as represented by the tube data, falls within the parameters established by the control data received from the memory section 42, an appropriate signal is transmitted from the comparator 44 to the control circuitry 46 which in turn supplies a signal to the operating means 48 to permit the pump initiation sequence to continue, ultimately resulting in normal operation of the pump.

However, should the tube data received from the RFID tag 26 be incompatible with any of the control data transmitted from the memory section 42, the signal transmitted to the operating means 48 will result in termination of the start-up sequence, so preventing operation of the pump. An appropriate message may be displayed on the screen 12, indicating the reason for the failure of the pump to operate. For example, the tube may be rejected so the pump fails to operate, if the wrong type of tube is fitted, if the tube has not been sterilized since its last use, or if the tube is unacceptably close to or beyond, its predicted operational life. If the run-time of the tube 4 exceeds the predicted operational life, this does not necessarily result in rejection of the tube 4. An alert may be generated to warn an operator that the predicted operational life has been exceeded. Failure or rejection in this instance is determined based on other parameters, for example, a maximum operational life specified for the tube 4, or operator identified failure of the tube 4.

The tube processing equipment 50 may comprise an autoclave as mentioned above, but may also comprise any other kind of apparatus which performs an operation on the tube 4 including molding equipment for initial production of the tube 4. The equipment 50 is provided with a data writer, which at the completion of an operation on the tube 4 writes to the memory 34 appropriate data relating to the process just completed. For example, in the initial production of the tube 4, the data may indicate the type of tube 4 and its individual identity along with the date of production. If the equipment 50 is an autoclave, the data may indicate that sterilization has been completed along with the date of the sterilizing operation. Thus the RFID tag 26 is equipped with all of the data required to enable the reader 28 to assess whether or not the tube 4 is appropriate for any particular pumping operation.

In addition, at the end of each period of operation of the pump the operating means 48 provides to the reader 28, data relating to parameters such as the duration, intensity (i.e. speed of rotation of the rotor), pressure, temperature and flowrate. This data is transmitted by the reader 28 to the RFID tag 26 to update data in the memory 34 relating to lifetime operation of the tube 4. Consequently, if a tube is nearing the end of its predicted operational life, the reader 28 can register this when the tube 4 is fitted. The reader 28 may then receive data related to the operation of the pump, and will be able to generate an appropriate signal if the remaining predicted life of the tube 4 is approaching. If this happens, an alert may be displayed on the screen 12, advising that the tube 4 needs to be replaced, and, ultimately, the pump may be shut down should continued use of the tube 4 entail a serious risk of tube failure.

When failure of the tube 4 occurs, the operational life of the tube 4 is compared against the predicted operational life stored in the control data memory section 42. If the operational life of the tube 4 falls outside a predetermined range/tolerance about the predicted operational life, the predicted operational life is recalculated to include the tube data representing the operational life of the tube 4.

Alternatively, the predicted operational life may be calculated each time a tube 4 fails without comparison of the operational life against the predicted operational life. The predicted operational life is thus recalculated as each tube fails as a moving average which is stored in the control data memory section 42.

In an alternative embodiment, predicted operational life data may be obtained from multiple pumps and made available to these or other pumps.

The invention claimed is:

1. A peristaltic pump comprising:
   a tube provided with a transponder having a data storage memory and means for transmitting tube data stored in the data storage memory; and
   a pump unit in which the tube is mounted, the pump unit having drive means for deforming the tube to perform a peristaltic action, and a reader for reading tube data transmitted from the transponder;
   wherein the reader comprises:
      tube data memory adapted to store the tube data transmitted from the transponder;
      a control data memory adapted to store control data relating to the tube;
      a comparator adapted to compare the tube data stored in the tube data memory and the control data stored in the control data memory;
   wherein the control data includes data representing the predicted operational life of the tube based on the average operational life for other tubes previously operated for their full operational life in the same environment, and wherein, when the tube fails, the comparator compares the operational life of the tube with the predicted operational life and updates the predicted operational life stored in the control data memory to include the operational life of the tube.

2. A peristaltic pump as claimed in claim 1, in which the reader is connected to
   operating means of the pump unit whereby operation of the pump unit is controlled in response to the tube data.

3. A peristaltic pump as claimed in claim 1, in which the tube data comprises
   data representing any one or more of:
      the identity of the tube;
      the size of the tube;
      the maximum pressure rating of the tube;
      the expiry date of the tube;
      the lot number of the tube;
      the maximum number of autoclave cycles of the tube;
      the default calibration of the tube; and
      the run-time of the tube.

4. A peristaltic pump as claimed in claim 2, wherein the comparator includes a processor for comparing tube data and control data and the operating means is controlled in response to a comparison of the tube data with the control data.

5. A peristaltic pump as claimed in claim 2, in which the operating means prevents operation of the drive means if the tube data is incompatible with the control data.

6. A peristaltic pump as claimed in claim 1, in which the control data comprises any one or more of:
   data representing the identity of the tube; and
   data representing processes conducted on the tube.

7. A peristaltic pump as claimed in claim 2, in which the reader is adapted to receive operation data from the operating means, and for converting the operation data to tube data.

8. A peristaltic pump as claimed in claim 7, in which the reader is provided with
   transmitting means for transmitting tube data, and in which the transponder is adapted to receive and store tube data transmitted from the reader.

9. A peristaltic pump as claimed in claim 7, in which the operation data comprises data representing duration and speed of operation of the pump unit.

10. A peristaltic pump as claimed in claim 9, in which the control data includes data representing maximum predicted tube life as a function of duration and speed of operation.

11. A peristaltic pump system comprising
   a peristaltic pump as claimed in claim 1, and
   tube processing equipment for performing a process on the tube, the tube processing equipment having a data writer for transmitting process data to the memory of the transponder of the tube, the process data being readable by the reader.

12. A peristaltic pump system as claimed in claim 11, in which the tube processing equipment is equipment for manufacturing the tube.

13. A peristaltic pump system as claimed in claim 11, in which the tube processing equipment is sterilizing equipment.

14. A method of operating a peristaltic pump as claimed in claim 1, the method comprising the steps of: (a) installing the tube in the pump unit so that the transponder and the reader are in communication with each other; (b) transmitting tube data from the transponder to the reader; (c) updating an accumulated operating time of the tube during operation of the pump; (d) operating the peristaltic pump until the tube reaches the end of its operational life; and (e) following the completion of step (d), updating the predicted operational life stored in the control data memory based on the operational life of the tube and of tubes previously operated for their full operational life in the same environment.

15. A method according to claim 14, wherein step (e) comprises updating the predicted operational life only when the operational life of the tube falls outside a predetermined range based on the predicted operational life held in the control data memory.

16. A method according to claim 14, wherein the previously operated tubes are tubes previously installed in and operated by the pump unit.

17. A method according to claim 14, wherein the predicted operational life is calculated as the average operational life of at least some of the previously operated tubes.

18. A method according to claim 14, in which step (b) comprises the step of transmitting tube data representing an accumulated operating time of the tube.

* * * * *